US009340837B2

(12) United States Patent
Bowers et al.

(10) Patent No.: US 9,340,837 B2
(45) Date of Patent: May 17, 2016

(54) METHODS AND KITS USEFUL IN THE DIFFERENTIATION OF *BURKHOLDERIA* SPECIES

(75) Inventors: Jolene Bowers, Flagstaff, AZ (US); David Engelthaler, Flagstaff, AZ (US); Paul Keim, Flagstaff, AZ (US)

(73) Assignees: THE TRANSLATIONAL GENOMICS RESEARCH INSTITUTE, Phoenix, AZ (US); ARIZONA BOARD OF REGENTS ON BEHALF OF NORTHERN ARIZONA UNIVERSITY, Flagstaff, AZ (US)

( * ) Notice: Subject to any disclaimer, the term of this patent is extended or adjusted under 35 U.S.C. 154(b) by 227 days.

(21) Appl. No.: 13/698,856

(22) PCT Filed: May 19, 2011

(86) PCT No.: PCT/US2011/037217
§ 371 (c)(1),
(2), (4) Date: May 13, 2013

(87) PCT Pub. No.: WO2011/146756
PCT Pub. Date: Nov. 24, 2011

(65) Prior Publication Data
US 2015/0252408 A1    Sep. 10, 2015

Related U.S. Application Data

(60) Provisional application No. 61/346,319, filed on May 19, 2010.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
CPC .......... *C12Q 1/689* (2013.01); *C12Q 2600/156* (2013.01)

(58) Field of Classification Search
None
See application file for complete search history.

(56) References Cited

U.S. PATENT DOCUMENTS

2004/0029129 A1*  2/2004  Wang .................. C07K 14/195
435/6.18

OTHER PUBLICATIONS

Wang et al., "Development and Evaluation of a Real-Time PCR Assay Targetting the Type III Secretion System of Burkholderia pseudomallei," Journal of Clinical Microbiology, 2006, vol. 44, No. 1, pp. 85-90.*
Ulrich et al., Using real-time PCR to specifically detect Burkholderia mallei. J Med Microbiol. 2006, vol. 55 (Pt 5), p. 551-559.
Andreadis et al., Use of immobilized PCR primers to generate covalently immobilized DNAs for in vitro transcription/translation reactions. Nucleic Acids Res. 2000, vol. 28(2):e5, pg. i-viii.

* cited by examiner

*Primary Examiner* — Young J Kim

(57) ABSTRACT

The invention pertains to sequences, methods, and kits useful in the identification of and differentiation between *Burkholderia pseudomallei* and *Burkholderia mallei*. The methods generally involve the addition of oligonucleotides to mixtures containing nucleic acid isolated from a sample and performing nucleic acid amplification on the mixture.

11 Claims, 4 Drawing Sheets

SEQUENCE LISTING

```
<160> NUMBER OF SEQ ID NOS: 4

<210> SEQ ID NO 1
<211> LENGTH: 20
<212> TYPE: DNA
<213> ORGANISM: Burkholderia mallei
<220> FEATURE:
<221> NAME/KEY: misc_feature
<223> OTHER INFORMATION: Forward Primer

<400> SEQUENCE: 1
atctgccgtg tcgagacgtt                                            20

<210> SEQ ID NO 2
<211> LENGTH: 20
<212> TYPE: DNA
<213> ORGANISM: Burkholderia pseudomallei
<220> FEATURE:
<221> NAME/KEY: misc_feature
<223> OTHER INFORMATION: Reverse Primer

<400> SEQUENCE: 2
caagtcgtgg atgcgcatta                                            20

<210> SEQ ID NO 3
<211> LENGTH: 15
<212> TYPE: DNA
<213> ORGANISM: Burkholderia mallei
<220> FEATURE:
<221> NAME/KEY: misc_feature
<223> OTHER INFORMATION: Bm Probe

<400> SEQUENCE: 3
ctgaaacgcg cagcg                                                 15

<210> SEQ ID NO 4
<211> LENGTH: 15
<212> TYPE: DNA
<213> ORGANISM: Burkholderia pseudomallei
<220> FEATURE:
```

-continued

```
<221> NAME/KEY: misc_feature
<223> OTHER INFORMATION: Bp Probe

<400> SEQUENCE: 4
ctgaaacgcg aagcg                                                   15
```

METHODS AND KITS USEFUL IN THE DIFFERENTIATION OF *BURKHOLDERIA* SPECIES

CROSS REFERENCE

This application is related to and claims the priority benefit of U.S. provisional application 61/346,319, filed on May 19, 2010, the teachings and content of which are incorporated by reference herein.

STATEMENT REGARDING FEDERALLY SPONSORED RESEARCH

This invention was made with government support under AI075568 awarded by the National Institutes of Health. The government has certain rights in this invention.

SEQUENCE LISTING

This application contains a sequence listing in computer readable format, the teachings and content of which are hereby incorporated by reference.

FIELD OF THE INVENTION

The present invention is related to methods useful in the identification of and differentiation between *Burkholderia pseudomallei* and *Burkholderia mallei*, two pathogens causing diseases.

BACKGROUND OF THE INVENTION

The bacterial species *Burkholderia pseudomallei* and *Burkholderia mallei*, though genetically very similar, have divergent lifestyles. *B. pseudomallei* is a soil saprophyte and facultative pathogen, causing the disease melioidosis, while *B. mallei* is an obligate pathogen, the etiological agent of disease glanders. Melioidosis is mostly a disease of humans and animals of Southeast Asia and Northern Australia, where *B. pseudomallei* is endemic in the soils. Infection mainly occurs upon inhalation or aspiration of the organism, or through open wounds. Clinical manifestations of melioidosis can be asymptomatic, localized to virtually any organ, or disseminated, though the primary presentations are pneumonia and sepsis, where mortality rates are significant. Glanders is mainly an equine disease found in much of the world, except for North America, Europe and Australia, with transmission to humans occurring primarily through direct contact with animals and aerosols. Clinical manifestations of glanders in humans are similar to those of melioidosis. Both species of bacteria are intrinsically resistant to several antibiotics and both are potential bioterrorism agents, deemed by the U.S. Centers for Disease Control and Prevention Category B Select Agents, for which no human vaccine is available. As such, the rapid detection and identification of these species is essential for immediate appropriate patient therapy and epidemiological surveillance or forensic investigation.

Identification of *B. pseudomallei* and *B. mallei* and diagnosis of melioidosis and glanders currently depends on time-consuming culture of the organism. Confirmation by biochemical assays can add a week onto definitive species identification without guarantee of accuracy. However, rapid biochemical assays have resulted in misdiagnosis of melioidosis, a mistake not easily detected due to the myriad clinical manifestations of the disease, and the lack of vigilance for these organisms in non-endemic regions. Serologic assays can be erroneous for multiple reasons. Serologic assays are contingent on a delayed immune response, and are useful only in non-endemic areas, where seroconversion due to previous exposure is improbable. Antigen-specific assays, including direct immunofluorescent microscopy and latex agglutination, have proven to be rapid and sensitive, but are not as yet available commercially.

BRIEF SUMMARY OF THE INVENTION

One aspect of the invention provides a method of determining the presence or absence of *B. mallei* in a sample. The method generally comprises the steps of: receiving a nucleic acid-containing sample from a subject; adding a first oligonucleotide to a mixture comprising said nucleic acid, said first oligonucleotide including a sequence selected from the group consisting of SEQ ID NO. 1, SEQ ID NO. 2, and SEQ ID NO. 3; subjecting the mixture to conditions that allow amplification of said nucleic acid; and identifying said sample as containing *B. mallei* or not containing *B. mallei* on the basis of a result of the nucleic acid amplification. In some forms of the invention when the first oligonucleotide in the method includes SEQ ID NO. 1, the method may further comprise the step of adding a second oligonucleotide including SEQ ID NO. 2 to said mixture. The general method may further comprise the step of performing DNA sequencing on a product of the nucleic acid amplification. In some forms of the invention, the general methods may further comprise the step of adding a third oligonucleotide including SEQ ID NO. 3 to said mixture. Preferably, the said third oligonucleotide will comprise a label. In some forms of the invention, the said label comprises a fluorescent label, preferably selected from the group consisting of FAM, dR110, 5-FAM, 6FAM, dR6G, JOE, HEX, VIC, TET, dTAMRA, TAMRA, NED, dROX, PET, BHQ+, Gold540, MGB, and LIZ. In some forms of the general method, the first oligonucleotide may be affixed to a solid substrate. The sample in this method can comprise an environmental sample. Alternatively or additionally, the sample may be derived from a subject selected from the group consisting of a human, a companion animal, and a livestock animal. Preferably, the said result in this method is in a form selected from the group consisting of a nucleic acid sequence and a ΔCt value Another aspect of the invention provides a method of determining the presence or absence of *B. pseudomallei* in a sample. The method generally comprises the steps of receiving a nucleic acid-containing sample from a subject; adding a first oligonucleotide to a mixture comprising said nucleic acid, said first oligonucleotide including a sequence selected from the group consisting of SEQ ID NO. 1, SEQ ID NO. 2, and SEQ ID NO. 4; subjecting said mixture to conditions that allow amplification of said nucleic acid; and identifying said sample as containing *B. pseudomallei* or not containing *B. pseudomallei* on the basis of a result of the nucleic acid amplification. In some forms of the invention, the said first oligonucleotide in this method includes SEQ ID NO. 1, and the method may further comprise the step of adding a second oligonucleotide including SEQ ID NO. 2 to said mixture. The method may further comprise the step of performing DNA sequencing on a product of the nucleic acid amplification. The method may further comprise the step of adding a third oligonucleotide including SEQ ID NO. 4 to said mixture. In some preferred forms, the said third oligonucleotide in this method comprises a label. In some forms of the invention, the said first oligonucleotide in this general method is affixed to a solid substrate. In some forms of the invention, the said nucleic acid-containing sample in this method comprises an environmental sample. Alternatively or additionally, the said sample is derived from a subject selected from the group consisting of a human, a companion animal, and a livestock animal. In some preferred forms of the invention, the said result in the general method is in a form selected from the group consisting of a nucleic acid sequence and a ΔCt value.

An additional aspect of the invention provides a method of determining whether a sample contains *B. mallei* or *B. pseudomallei*, and the method generally comprises the steps of: receiving said sample, wherein said sample comprises nucleic acid; forming a mixture by adding oligonucleotides represented by SEQ ID NO. 1, SEQ ID NO. 2, SEQ ID NO. 3, and SEQ ID NO. 4 to said nucleic acid; subjecting said mixture to conditions that allow amplification of said nucleic acid; and identifying said sample as containing or not containing *B. mallei* or *B. pseudomallei* based upon a result of the nucleic acid amplification. The method may further comprise the step of performing DNA sequencing upon one or more products of the nucleic acid amplification. In some preferred forms of the invention, the said oligonucleotide represented by SEQ ID NO. 3 in the general method comprises a first label and the said oligonucleotide represented by SEQ ID NO. 4 comprises a second label, preferably different from said first label. In some forms of the invention, the said first oligonucleotide in this method is affixed to a solid substrate. In some forms of the invention, the said sample in this method comprises an environmental sample. Alternatively or additionally, the said sample is derived from a subject selected from the group consisting of a human, a companion animal, and a livestock animal. In some forms, the said result of the method comprises one or more DNA sequences. Alternatively or additionally, the result of the method may comprise one or more ΔCt values.

Another aspect of the present invention further provides a kit that facilitates determining whether a nucleic acid-containing sample contains *B. mallei* or *B. pseudomallei*. Generally the kit comprises: a first oligonucleotide represented by SEQ ID NO. 1; a second oligonucleotide represented by SEQ ID NO. 2; and an indication of a result that signifies classification of the sample as containing a bacteria selected from the group consisting of *B. mallei* and *B. pseudomallei* when said nucleic acid from said sample is mixed with said first and said second oligonucleotides. The kit may further comprise a third oligonucleotide including a sequence selected from the group consisting of SEQ ID NO. 3 and SEQ ID NO. 4. The said first oligonucleotide of the kit is affixed to a substrate in some forms of the invention. The said result provided by the components of the kit can be in a form selected from the group consisting of a ΔCt value and a nucleic acid sequence. In some forms of the invention, the said indication of the kit is selected from the group consisting of a positive control, a writing, and software configured to detect the result as input and identification of the sample as containing *B. mallei* or *B. pseudomallei* as output.

Still another aspect of the invention provides an isolated sequence having at least 95%, more preferably at least 96%, still more preferably at least 97%, even more preferably at least 98%, still more preferably at least 99%, and even more preferably at least 99.5% sequence identity with a sequence selected from the group consisting of SEQ ID NO. 1, SEQ ID NO. 2, SEQ ID NO. 3, SEQ ID NO. 4, and amplification products thereof. The isolated sequence may further comprise a label attached to said sequence. Preferred labels are as described above.

Other aspects and features of the disclosure are described more thoroughly below.

Figure 1:
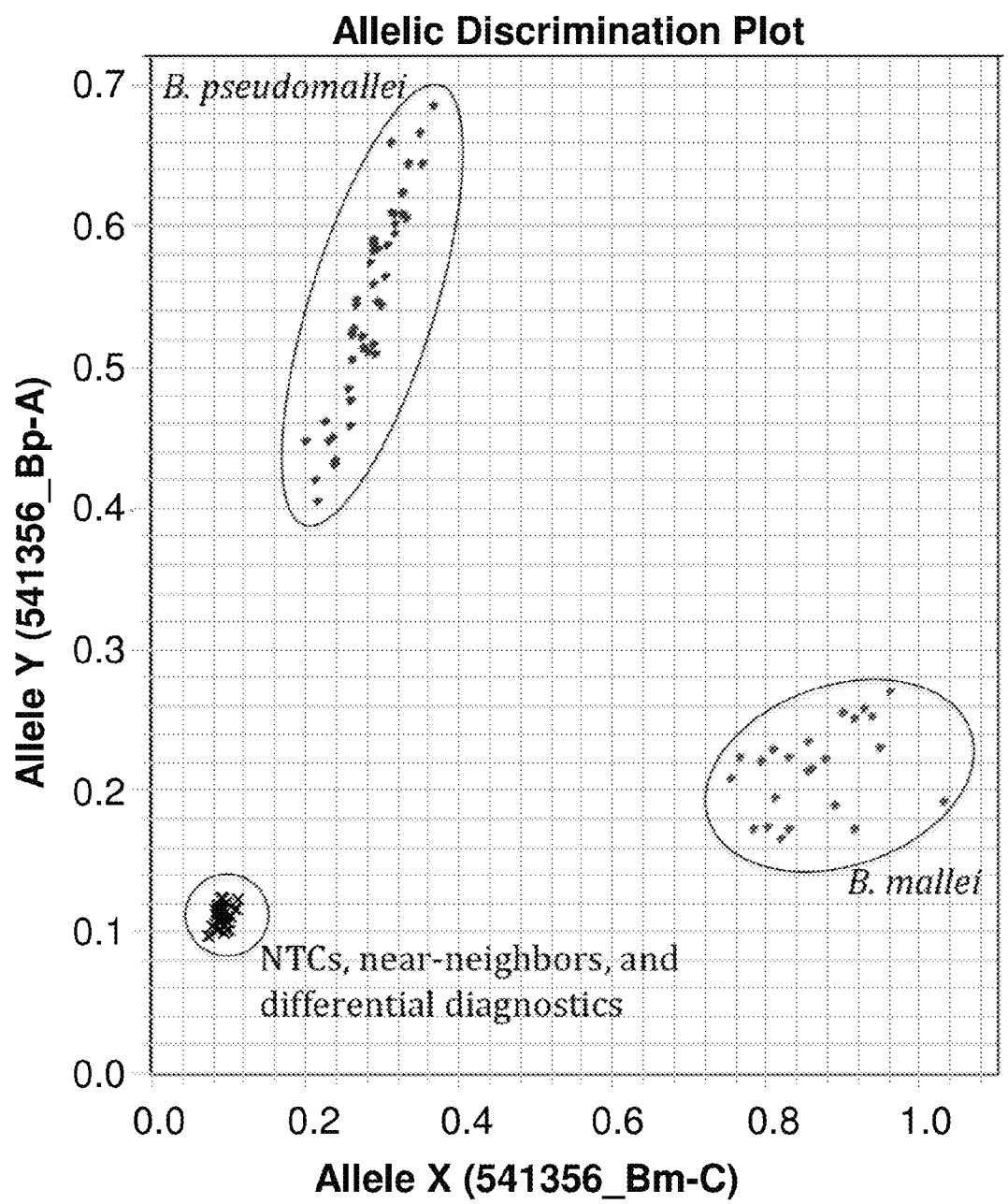
FIG. 1 depicts the results by Allelic Discrimination Plot, from using BurkDiff across 45 *B. pseudomallei* and 23 *B. mallei* strains. Also included are 2 no template controls (NTCs), and 26 near-neighbor and differential diagnostic species;

FIG. 2 depicts results of 8 replicates of serially diluted *B. pseudomallei* and *B. mallei* using Allelic Discrimination Plot. Note that 4 of the 8 replicates at the $10^1$ copy template amount did not amplify for either the *B. pseudomallei* or the *B. mallei* strains;

FIG. 3 depicts results of quadruplicate analysis of a 10-fold serial dilution of DNA extracted by crude heat lysis method from *B. pseudomallei* strain 2002721637. Note that 2 of the 4 replicates did not amplify at the $10^1$ copy template amount; and FIG. 4 depicts results of quadruplicate analysis of a 10-fold serial dilution of DNA extracted by crude heat lysis method from *B. mallei* strain 2002734303. Note that 2 of the 4 replicates did not amplify at the $10^1$ copy template amount for *B. mallei*.

DETAILED DESCRIPTION OF THE INVENTION

Any compositions of matter disclosed herein are identified by a particular nucleic acid sequence. However, the invention contemplates any sequence similar enough to the listed sequence still able to bind sufficiently to the sample sequence that the conjugate sequence is identified, and/or the targeted polynucleotide is amplified through a nucleic acid amplification method. Therefore, the identifying sequence may include a deletion, insertion, SNP, substitution. A sequence having at least 60%, 70%, 80%, 90%, 95%, 96%, 97%, 98%, 99%, or 99.5% identity to the identifying sequence is still encompassed by the invention.

"Sequence Identity" as it is known in the art refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences. As an illustration, by a polynucleotide having a nucleotide sequence having at least, for example, 85%, preferably 90%, even more preferably 95% "sequence identity" to a reference nucleotide sequence, it is intended that the nucleotide sequence of the given polynucleotide is identical to the reference sequence except that the given polynucleotide sequence may include up to 15, preferably up to 10, even more preferably up to 5 point mutations per each 100 nucleotides of the reference nucleotide sequence. In other words, in a polynucleotide having a nucleotide sequence having at least 85%, preferably 90%, even more preferably 95% identity relative to the reference nucleotide sequence, up to 15%, preferably 10%, even more preferably 5% of the nucleotides in the reference sequence may be deleted or substituted with another nucleotide, or a number of nucleotides up to 15%, preferably 10%, even more preferably 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence. Analogously, by a polypeptide having a given amino acid sequence having at least, for example, 85%, preferably 90%, even more preferably 95% sequence identity to a reference amino acid sequence, it is intended that the given amino acid sequence of the polypeptide is identical to the reference sequence except that the given polypeptide sequence may include up to 15, preferably up to 10, even more preferably up to 5 amino acid alterations per each 100 amino acids of the reference amino acid sequence. In other words, to obtain a given polypeptide sequence having at least 85%, preferably 90%, even more preferably 95% sequence identity with a reference amino acid sequence, up to 15%, preferably up to 10%, even more preferably up to 5% of the amino acid residues in the reference sequence may be deleted or substituted with another amino acid, or a number of amino acids up to 15%, preferably up to 10%, even more preferably up to 5% of the total number of amino acid residues in the reference sequence may be inserted into the reference sequence. These alterations of the reference sequence may occur at the amino or the carboxy terminal positions of the reference amino acid sequence or anywhere between those terminal positions, interspersed either individually among residues in the reference sequence or in the one or more contiguous groups within the reference sequence. Preferably, residue positions which are not identical differ by conservative amino acid substitutions. However, conservative substitutions are not included as a match when determining sequence identity.

An allele includes any form of a particular nucleic acid that may be recognized as a form of the particular nucleic acid on account of its location, sequence, epigenetic modification or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene sequence, whether alone or in combination. The presence or absence of an allele may be detected through the use of any process through which a specific nucleic acid molecule may be detected, including direct and indirect methods of detecting the presence or absence of an allele. Different alleles may or may not encode proteins or peptides. Different alleles may differ in expression level, pattern temporal, or spatial specificity and expression regulation. In case of encoded proteins, the protein from different alleles may or may not be functional. Further, the protein may be gain-of-function, loss-of-function, or with altered function. An allele may also be called a mutation or a mutant. An allele may be compared to another allele that may be termed a wild type form of an allele. In some cases, the wild type allele is more common than the mutant.

A sample may be derived from anywhere that a *Burkholderia* spp. may be found including soil, air, water, solid surfaces (whether natural or artificial), culture media, foodstuffs, and any interfaces between or combinations of these elements. Additionally, a sample may be derived from a subject, such as a plant, insect, or animal, including humans. Samples derived from animals include but are not limited to biopsy or other in vivo or ex vivo analysis of prostate, breast, skin, hair, muscle, facia, brain, endometrium, lung, head and neck, pancreas, small intestine, blood, liver, testes, ovaries, colon, skin, stomach, esophagus, spleen, lymph node, bone marrow, kidney, placenta, or fetus. Samples derived from subjects may also take the form of a fluid sample such as peripheral blood, lymph fluid, ascites, serous fluid, pleural effusion, sputum, bronchial wash, bronchioalveolar lavage fluid (BALF,) cerebrospinal fluid, semen, amniotic fluid, lacrimal fluid, stool, urine, or from any other fluid source in which *Burkholderia* might be present. Samples collected from a plant may be collected from part of a plant or from an entire plant. Samples may be collected by any method now known or yet to be disclosed, including swiping or swabbing an area or orifice, removal of a piece of tissue as in a biopsy, or any method known to collect bodily fluids. Samples may be suspected of containing bacteria if they are derived from a subject displaying symptoms of a bacterial infection or from an environmental sample from an area in which bacteria is thought to be endemic.

Direct methods of detecting the presence of an allele include but are not limited to any form of DNA sequencing including Sanger, next generation sequencing, pyrosequencing, SOLID sequencing, massively parallel sequencing, pooled, and bar coded DNA sequencing or any other sequencing method now known or yet to be disclosed; PCR-based methods such as real-time PCR, quantitative PCR, reverse transcription PCR or any combination of these; allele specific ligation; comparative genomic hybridization; or any other method that allows the detection of a particular nucleic acid sequence within a sample or enables the differentiation of a first nucleic acid from a second nucleic acid that differs from the first nucleic acid by one or more nucleotides. A sample may be suspected of including a nucleic acid from bacteria of interest. Nucleic acids may include but need not be limited to genomic DNA, cDNA, mRNA, tRNA, mitochondrial DNA, plasmid DNA, siRNA, shRNA, genomic DNA, or any other naturally occurring or artificial nucleic acid molecule. A subject may be any organism that may be infected by bacteria including plants, such as chordates, mammals, insects, endangered species, or any other organism of agricultural, environmental, or other significance.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP) are added to each of four reactions (one reaction for each of the chain terminator bases). The sequence may be determined by electrophoresis of the resulting strands. In dye terminator sequencing, each of the chain termination bases is labeled with a fluorescent label of a different wavelength which allows the sequencing to be performed in a single reaction.

In pyrosequencing, the addition of a base to a single stranded template to be sequenced by a polymerase results in the release of a pyrophosphate upon nucleotide incorporation. An ATP sulfyrlase enzyme converts pyrophosphate into ATP which in turn catalyzes the conversion of luciferin to oxyluciferin which results in the generation of visible light that is then detected by a camera.

In SOLID sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted DNA is attached to a surface. The fragments are extended and bridge amplified to create a flow cell with clusters, each with a plurality of copies of a single fragment sequence. The templates are sequenced by synthesizing the fragments in parallel. Bases are indicated by the release of a fluorescent dye correlating to the addition of the particular base to the fragment.

When a nucleic acid includes a particular sequence, the sequence may be a part of a longer nucleic acid or may be the entirety of the sequence. The nucleic acid may contain nucleotides 5' of the sequence, 3' of the sequence, or both. The concept of a nucleic acid including a particular sequence further encompasses nucleic acids that contain less than the full sequence that are still capable of specifically detecting an allele. Nucleic acid sequences may be identified by the IUAPC letter code which is as follows: A—Adenine base; C—Cytosine base; G—guanine base; T or U—thymine or uracil base. M-A or C; R-A or G; W-A or T; S-C or G; Y-C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A sequence having less than 60% 70%, 80%, 90%, 95%, 96%, 97%, 98%, 99%, 99.5% or 100% identity to the identifying sequence may still be encompassed by the invention if it is capable of binding to its complimentary sequence and/or facilitating nucleic acid amplification of a desired target sequence. If a sequence is represented in degenerate form; for example through the use of codes other than A, C, G, T, or U; the concept of a nucleic acid including the sequence also encompasses a mixture of nucleic acids of different sequences that still meet the conditions imposed by the degenerate sequence.

Indirect methods of detecting an allele generally involve assessing the expression of a genomic DNA in the form of mRNA or protein. Such expression may be assessed by any of a number of methods used currently in the art and yet to be developed. Examples include any nucleic acid detection method including the following nonlimiting examples, microarray analysis, RNA in situ hybridization, RNAse protection assay, Northern blot, RT-PCR (real-time PCR), and quantitative PCR, and QRTPCR (Quantitative Real-Time PCR). Other examples include any process of detecting expression that uses an antibody including the following nonlimiting examples, flow cytometry, immunohistochemistry, ELISA, Western blot, Northwestern blot, and immunoaffinity chromatography. Antibodies may be monoclonal, polyclonal, or any antibody fragment including an Fab, $F(ab)_2$, Fv, scFv, phage display antibody, peptibody, multispecific ligand, or any other reagent with specific binding to a target. Other methods of assessing protein expression include the following nonlimiting examples: HPLC, mass spectrometry, protein microarray analysis, PAGE analysis, isoelectric focusing, 2-D gel electrophoresis, and enzymatic assays.

A nucleic acid may be added to a sample by any of a number of methods including manual methods, mechanical methods, or any combination thereof. The presence of the allele may be signified by any of a number of methods including amplification of a specific nucleic acid sequence, sequencing of a native or amplified nucleic acid, or the detection of a label either bound to or released from the nucleic acid. Addition of the nucleic acid to the sample also encompasses addition of the nucleic acid to a sample in which the target allele to which the nucleic acid has specificity is absent.

In some aspects of the invention, the presence of an allele may be established by binding to a microarray such as a DNA chip. Examples of DNA chips include chips in which a number of single stranded oligonucleotide probes are affixed to a solid substrate such as silicon glass. Oligonucleotides with a sequence complementary to an allele are capable of specifically binding to that allele to the exclusion of alleles that differ from the specific allele by one or more nucleotides. Labeled sample DNA is hybridized to the oligonucleotides and detection of the label is correlated with binding of the sample and consequently the presence of the allele in the sample.

In allele-specific hybridization, oligonucleotide sequences representing all possible variations at a polymorphic site are included on a chip. The chip and sample are subjected to conditions under which the labeled sample DNA will bind only to an oligonucleotide with an exact sequence match. In allele-specific primer extension, sample DNA hybridized to the chip may be used as a synthesis template with the affixed oligonucleotide as a primer. Under this method, only the added dNTP's are labeled. Incorporation of the labeled dNTP then serves as the signal indicating the presence of the allele. The fluorescent label may be detected by any of a number of instruments configured to read fluorescent labels on a DNA chip. Preferably, these instruments will be capable of reading at least four different fluorescent labels. In another alternative, the identity of the final dNTP added to the oligonucleotide may be assessed by mass spectrometry. In this alternative, the dNTP's may, but need not be, labeled with a label of known molecular weight.

A nucleic acid probe may be affixed to a substrate. In other aspects of the invention, a sample may be affixed to the substrate. A probe or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi solid material onto which a probe may be affixed, attached or printed, either singly or in the presence of one or more additional probes or samples as is exemplified in a microarray. Examples of substrate materials include but are not limited to polyvinyl, polystyrene, polypropylene, polyester or any other plastic, glass, silicon dioxide or other silanes, hydrogels, gold, platinum, microbeads, micelles and other lipid formations, nitrocellulose, or nylon membranes. The substrate may take any form, including a spherical bead or flat surface. For example, the probe may be bound to a substrate in the case of an array or an in situ PCR reaction. The sample may be bound to a substrate in the case of a Southern Blot.

A nucleic acid probe may include a label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent), stain, enzyme, or nonradioactive metal. Specific examples include but are not limited to: fluorescein, biotin, digoxigenin, alkaline phosphatese, biotin, streptavidin, $^3$H, $^{14}$C, $^{32}$P, $^{35}$S, or any other compound capable of emitting radiation, rhodamine, 4-(4'-dimethylamino-phenylazo)benzoic acid ("Dabcyl"), 4-(4'-dimethylamino-phenylazo)sulfonic acid (sulfonyl chloride) ("Dabsyl"), 5-((2-aminoethyl)-amino)-naphtalene-1-sulfonic acid ("EDANS"), Psoralene derivatives, haptens, cyanines, acridines, fluorescent rhodol derivatives, cholesterol derivatives, ethylenediaminetetraacetic acid ("EDTA") and derivatives thereof, or any other compound that may be differentially detected. The label may also include one or more fluorescent dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, BHQ+, Gold 540, MGB and LIZ.

In some aspects of the invention, the allele may be detected by quantitative PCR analysis, which may be performed using a kit containing components that facilitate genotyping analysis. Genotyping analysis may be performed using a probe that is capable of hybridizing to a nucleic acid sequence of interest. Probes may include nucleic acids, oligonucleotides (DNA, or RNA), proteins, protein complexes, conjugates, natural ligands, small molecules, nanoparticles, or any combination of molecules that includes one or more of the above, or any other molecular entity capable of specific binding to a any allele, whether such molecular entity exists now or is yet to be disclosed. In one aspect of the invention, the probe comprises an oligonucleotide. The concept of oligonucleotides includes any DNA or RNA molecule of two or more nucleotides, whether from a natural source, artificially synthesized, or produced through the use of recombinant DNA technology. A nucleotide is an individual deoxyribonucleotide or ribonucleotide base. Examples of nucleotides include but are not limited to: adenine, thymine, guanine, cytosine, and uracil which may be abbreviated as A, T, G, C, or U in representations of oligonucleotide sequence. The length of the oligonucleotide depends on how the oligonucleotide will be used. One skilled in the art would understand the approximate length of oligonucleotide necessary for use in any given method. Depending on the method, an oligonucleotide may be 0 to 1000 bases in length. In other aspects, it may be 5 to 500 bases in length, 5 to 100 bases in length, 5 to 50 bases in length, or 10 to 30 bases in length.

Nucleic acids that may be subjected to amplification may be from any source. In general, nucleic acid amplification is a process by which copies of a nucleic acid may be made from a source nucleic acid. In some nucleic amplification methods, the copies are generated exponentially. Examples of nucleic acid amplification include but are not limited to: the polymerase chain reaction (PCR), ligase chain reaction (LCR,) self-sustained sequence replication (3SR), nucleic acid sequence based amplification (NASBA,) strand displacement amplification (SDA), amplification with Qβ replicase, whole genome amplification with enzymes such as φ29, whole genome PCR, in vitro transcription with Klenow or any other RNA polymerase, or any other method by which copies of a desired sequence are generated.

Polymerase chain reaction (PCR) is a particular method of amplifying DNA, generally involving the mixing of a nucleic sample, two or more primers, a DNA polymerase, which may be a thermostable DNA polymerase such as Taq or Pfu, and deoxyribose nucleoside triphosphates (dNTP's). In general, the reaction mixture is subjected to temperature cycles comprising a denaturation stage, (typically 80-100° C.) an annealing stage with a temperature that may be based on the melting temperature (Tm) of the primers and the degeneracy of the primers, and an extension stage (for example 40-75° C.) In real-time PCR analysis, additional reagents, methods, optical detection systems, and devices are used that allow a measurement of the magnitude of fluorescence in proportion to concentration of amplified DNA. In such analyses, incorporation of fluorescent dye into the amplified strands or labeled probes that bind to a specific sequence during the annealing phase and release their fluorescent tags during the extension phase may be detected. Either of these will allow a detection and quantification of the amount of specific DNA present in the initial sample. RNA may be detected by PCR analysis by creating a DNA template from RNA through a reverse transcriptase enzyme.

Kits that facilitate nucleic acid based methods may further include one or more of the following: specific nucleic acids such as oligonucleotides, labeling reagents, enzymes including PCR amplification reagents such as the DNA polymerases Taq or Pfu, reverse transcriptase, or one or more other polymerases, and/or reagents that facilitate hybridization. Specific nucleic acids may include nucleic acids, polynucleotides, oligonucleotides (DNA, or RNA), or any combination of molecules that includes one or more of the above, or any other molecular entity capable of specific binding to a nucleic acid marker. In one aspect of the invention, the specific nucleic acid comprises one or more oligonucleotides capable of hybridizing to the marker.

A specific nucleic acid may include a label. A label may be any substance capable of aiding a machine, detector, sensor, device, or enhanced or unenhanced human eye from differentiating a sample that that displays positive expression from a sample that displays reduced expression. Examples of labels include but are not limited to: a radioactive isotope or chelate thereof, a dye (fluorescent or nonfluorescent), stain, enzyme, or nonradioactive metal. Specific examples include but are not limited to: fluorescein, biotin, digoxigenin, alkaline phosphatase, biotin, streptavidin, $^3$H, $^{14}$C, $^{32}$P, $^{35}$S, or any other compound capable of emitting radiation, rhodamine, 4-(4'-dimethylaminophenylazo)benzoic acid ("Dabcyl"), 4-(4'-dimethylamino-phenylazo)sulfonic acid (sulfonyl chloride) ("Dabsyl"), 5-((2-aminoethyl)-amino)-naphtalene-1-sulfonic acid ("EDANS"), Psoralen derivatives, haptens, cyanines, acridines, fluorescent rhodol derivatives, cholesterol derivatives; ethylene diamine tetra-acetic acid ("EDTA") and derivatives thereof, or any other compound that signals the presence of the labeled nucleic acid. In one embodiment of the invention, the label includes one or more dyes optimized for use in genotyping. Examples of such dyes include but are not limited to: dR110, 5-FAM, 6FAM, dR6G, JOE, HEX, VIC, TET, dTAMRA, TAMRA, NED, dROX, PET, BHQ+, Gold 540, MGB and LIZ.

An oligonucleotide may be any polynucleotide having a length of at least 2 nucleotides. Oligonucleotides may be less than 10, less than 15, less than 20, less than 30, less than 40, less than 50, less than 75, less than 100, less than 200, or less than 500 nucleotides in length. While oligonucleotides are often linear, they may, depending on their sequence and conditions, assume a two- or three-dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

A nucleotide is an individual deoxyribonucleotide or ribonucleotide base. Examples of nucleotides include but are not limited to: adenine, thymine, guanine, cytosine, and uracil, which may be abbreviated as A, T, G, C, or U in representations of oligonucleotide or polynucleotide sequence. Any molecule of one or more nucleotide bases, whether DNA or RNA, may be termed a nucleic acid.

A nucleic acid reagent used to detect to an allele may be affixed to a solid substrate. Alternatively, the sample may be affixed to a solid substrate and the nucleic acid reagent placed into a mixture. For example, the nucleic acid reagent may be bound to a substrate in the case of an array or the sample may be bound to a substrate as the case of a Southern Blot, Northern blot or other method that affixes the sample to a substrate. A nucleic acid reagent or sample may be covalently bound to the substrate or it may be bound by some non covalent interaction including electrostatic, hydrophobic, hydrogen bonding, Van Der Waals, magnetic, or any other interaction by which a probe such as an oligonucleotide probe may be attached to a substrate while maintaining its ability to recognize the allele to which it has specificity. A substrate may be any solid or semi solid material onto which a probe may be affixed, attached or printed, either singly or in the formation of a microarray. Examples of substrate materials include but are not limited to polyvinyl, polysterene, polypropylene, polyester or any other plastic, glass, silicon dioxide or other silanes, hydrogels, gold, platinum, microbeads, micelles and other lipid formations, nitrocellulose, or nylon membranes. The substrate may take any shape, including a spherical bead or flat surface.

A kit may also contain an indication that links the output of the kit to a particular result. For example, an indication may be one or more sequences or that signify the identification of a Burkholderia species. A kit may contain a standard curve configured to quantify the amount of Burkholderia present in a sample. An indication includes any guide that links the output of the kit to a particular result. The indication may be a particular sequence, a particular ΔCt level in a qRTPCR reaction or a range thereof, a level of fluorescence or radioactive decay, a value derived from a standard curve, or from a control, or any combination of these and other outputs. The indication may be printed on a writing that may be included in the kit or it may be posted on the Internet or embedded in a software package.

Example

As disclosed herein, an allelic discrimination assay, referred to as BurkDiff, provides a high level of specificity for accurate species identification.

23 *B. pseudomallei* and 10 *B. mallei* genomes were compared to search for shared orthologous SNPs. 1,235 SNPs were identified to have shared character states among all *B. mallei* genomes that differ from the character state shared by all *B. pseudomallei* genomes. The 1,235 SNPs were further filtered by using a mismatch value of 100 (i.e., the nearest SNP was at least 100 bases away), resulting in a pool of 74 SNPs. A GenBank BLAST search of a subset of the SNPs and their flanking regions revealed the exclusivity of one of the regions to *B. pseudomallei* and *B. mallei*, so it was selected for assay development and validation.

Using Primer Express 3.0 software (Life Technologies, Foster City, Calif.), a Taqman SNP dual-probe allelic discrimination assay was designed in which one first probe (5'-CTGAAACGCGCAGCG-3'; SEQ ID NO: 3) was designed to hybridize with the *B. mallei* allele, and a second probe (5'-CTGAAACGCGAAGCG-3'; SEQ ID NO: 4) was designed to hybridize to the *B. pseudomallei* allele. The first probe was labeled with FAM at the 5' end and MGB at the 3' end. The second probe was labeled with VIC at the 5' end and MGB at the 3' end. The first probe was used to detect "state C", indicating the identity of the *Burkholderia* bacteria as *B. mallei*. The second probe was used to detect "state A", indicating the identity of the *Burkholderia* bacteria as *B. pseudomallei*. Real-time PCR was carried out in 10 uL reactions containing 900 nM of both forward (5'-CGAGCG-CATCGTACTCGTA-3'; SEQ ID NO: 1) and reverse (5'-CAAGTCGTGGATGCGCATTA-3'; SEQ ID NO: 2) primers, 200 nM of each probe, 1× Applied Biosystems Genotyping Mastermix, and 0.5 ng template. Thermal cycling and endpoint analysis was performed on an AB 7900HT sequence detection system (Life Technologies) using the following conditions: 50° C. for 2 min, 95° C. for 10 min, and 40 cycles at 95° C. for 15 s and at 58° C. for 1 min.

To evaluate the utility of this SNP and its locus as a diagnostic marker for *B. pseudomallei* and *B. mallei*, the Taqman allelic discrimination assay was used to genotype a collection of human, animal, and environmental isolates of *B. pseudomallei* (n=469) and *B. mallei* (n=49) from a broad geographic range (Table 1). The specificity of the assay was further assessed by screening isolates of near-neighbor species (n=62), and isolates of species of similar clinical presentation or normal flora (n=328) (Table 2). All isolates were originally identified by standard microbiological techniques in the laboratory of origin. Out of the isolates screened with the Taqman assay, all 469 *B. pseudomallei* strains were shown to contain the allele with the SNP state A, and all 49 *B. mallei* strains were shown to contain that with the SNP state C (Table 1). No amplification of DNA from the 390 non-target species was detected, including the *B. oklahomensis* and the *B. thailandensis*-like strain MSMB43, both of which cross-reacted with a previously published allelic discrimination assay (62 non-target species in Table 1, and 328 non-target species in Table 2). The results were further depicted by Allelic Discrimination Plot in FIG. 1, in which the BurkDiff assay was performed across 45 *B. pseudomallei* and 23 *B. mallei* strains, and two No Template Controls (NTCs), and 26 near-neighbor and differentia diagnostic species. As shown in Table 1, 2 and FIG. 1, the BurkDiff assay is highly reliable and accurate.

TABLE 1

*B. pseudomallei*, *B. mallei*, and genetic near-neighbor isolates used in this study.

| Species | Country | Isolated from | No. of isolates | TaqMan result (allele) |
|---|---|---|---|---|
| *B. mallei* | China | Human | 2 | C |
| | China | Animal | 4 | C |
| | China | Unknown | 2 | C |
| | France | Unknown | 1 | C |
| | Hungary | Animal | 1 | C |
| | Hungary | Unknown | 1 | C |
| | India | Animal | 3 | C |
| | India | Unknown | 1 | C |
| | Pakistan | Unknown | 6 | C |
| | Turkey | Human | 4 | C |
| | Turkey | Animal | 1 | C |
| | Turkey | Unknown | 10 | C |
| | UK | Unknown | 1 | C |
| | USA | Human | 4 | C |
| | USA | Animal | 1 | C |
| | USA | Unknown | 3 | C |
| | Unknown | Animal | 2 | C |
| | Unknown | Unknown | 2 | C |
| Total | 8 | | 49 | |
| *B. pseudomallei* | Australia | Human | 131 | A |
| | Australia | Animal | 10 | A |
| | Australia | Environmental | 57 | A |
| | Australia | Unknown | 6 | A |
| | USA | Human | 6 | A |
| | Bangladesh | Human | 2 | A |
| | Cambodia | Unknown | 2 | A |
| | China | Unknown | 3 | A |
| | Ecuador | Human | 2 | A |
| | Ecuador | Animal | 1 | A |
| | Fiji | Human | 1 | A |
| | India | Unknown | 1 | A |
| | Indonesia | Environmental | 1 | A |
| | Kenya | Human | 1 | A |
| | Kenya | Environmental | 2 | A |
| | Laos | Unknown | 2 | A |
| | Madagascar | Environmental | 2 | A |
| | Malaysia | Human | 2 | A |
| | Malaysia | Environmental | 3 | A |
| | Malaysia | Unknown | 15 | A |
| | Mauritius | Human | 1 | A |
| | Pakistan | Human | 2 | A |
| | Papua New Guinea | Human | 1 | A |
| | Papua New Guinea | Unknown | 1 | A |
| | Puerto Rico | Human | 2 | A |
| | Singapore | Human | 2 | A |
| | Singapore | Environmental | 1 | A |
| | Sweden | Human | 1 | A |
| | Thailand | Human | 89 | A |
| | Thailand | Environmental | 105 | A |
| | Unknown | Human | 1 | A |
| | Unknown | Environmental, soil | 2 | A |
| | Unknown | Unknown | 2 | A |
| | Venezuela | Human | 1 | A |
| | Vietnam | Human | 4 | A |
| | Vietnam | Animal | 1 | A |
| | Vietnam | Unknown | 3 | A |
| Total | 22 | | 469 | |
| *B. cepacia* | USA | | 2 | Negative |
| *B. oklahomensis* | USA | | 2 | Negative |
| *B. thailandensis* | | | 58 | Negative |
| Total | | | 62 | |

TABLE 2

Differential diagnostic and background flora isolates of approximately 80 species screened across BurkDiff to validate the assay's specificity. None of these isolates amplified.

| Species | No. of isolates |
|---|---|
| *Abiotrophia/Granulicatella* grp | 1 |
| *Achromobacter xylosoxidans* | 1 |
| *Acinetobacter baumanni* | 7 |
| *Bacillus anthracis* | 1 |
| *Bacillus cereus* | 1 |
| *Bacillus* sp. | 2 |
| *Bacteroides fragilis* | 1 |
| *Bacteroides uniformis* | 1 |
| *Bordetella bronchiseptica* | 1 |
| *Brucella abortus* | 1 |
| *Brucella suis* | 1 |
| *Candida albicans* | 5 |
| *Candida glabrata* | 2 |
| *Candida parapsilosis* | 3 |
| *Candida tropicalis* | 1 |
| *Chryseobacterium indologenes* | 1 |
| Coagulase negative *Staphylococcus* | 16 |
| *Coccidioides immitis* | 1 |
| *Coccidioides posadasii* | 2 |
| *Corynebacterium diphtheriae* | 1 |
| *Corynebacterium jeikeium* | 1 |
| *Coxiella burnetii* | 2 |
| *Enterobacter aerogenes* | 2 |
| *Enterobacter cloacae* | 10 |
| *Enterococcus faecalis* | 9 |
| *Enterococcus faecium* | 6 |
| *Escherichia coli* | 11 |
| *Francisella tularensis* | 2 |
| *Haemophilus Influenzae* | 4 |
| *Haemophilus parainfluenzae* | 2 |
| Human gDNA | 2 |
| *Klebsiella oxytoca* | 1 |
| *Klebsiella pneumoniae* | 8 |
| *Lactococcus lactis* | 1 |
| *Legionella pneumophila* | 1 |
| *Listeria monocytogenes* | 1 |
| *Micrococcus* sp. | 1 |
| *Moraxella catarrhalis* | 7 |
| *Mycobacterium avium* | 1 |
| *Mycoplasma pneumoniae* | 1 |
| *Neisseria gonorrhoeae* | 4 |
| *Neisseria meningitidis* | 3 |
| *Pasteurella multocida* | 1 |
| *Propionibacterium* sp. | 1 |
| *Providencia stuartii* | 1 |
| *Pseudomonas aeruginosa* | 7 |
| *Rhizopus oryzae* | 1 |
| *Rothia mucilaginosa* | 1 |
| *Salmonella enterica* | 1 |
| *Shigella dysenteriae* | 1 |
| *Staphylococcus arlettae* | 1 |
| *Staphylococcus aureus* | 55 |
| *Staphylococcus capitis* | 1 |
| *Staphylococcus cohnii* | 1 |
| *Staphylococcus epidermidis* | 8 |
| *Staphylococcus equorum* | 1 |
| *Staphylococcus gallinarum* | 1 |
| *Staphylococcus haemolyticus* | 3 |
| *Staphylococcus hominis* | 1 |
| *Staphylococcus kloosii* | 1 |
| *Staphylococcus lugdunensis* | 1 |
| *Staphylococcus saprophyticus* | 2 |
| *Staphylococcus xylosus* | 3 |
| *Stenotrophomonas maltophilia* | 1 |
| *Streptococcus agalactiae* | 9 |
| *Streptococcus anginosus* | 2 |
| *Streptococcus equi* | 1 |
| *Streptococcus gordonii* | 1 |
| *Streptococcus mitis* | 2 |
| *Streptococcus mutans* | 1 |
| *Streptococcus oralis* | 1 |
| *Streptococcus pneumoniae* | 56 |
| *Streptococcus pyogenes* | 13 |
| *Streptococcus salivarius* | 2 |

TABLE 2-continued

Differential diagnostic and background flora isolates of approximately 80 species screened across BurkDiff to validate the assay's specificity. None of these isolates amplified.

| Species | No. of isolates |
|---|---|
| *Streptococcus thermophilus* | 1 |
| *Streptococcus uberis* | 1 |
| *Streptococcus viridans* grp | 8 |
| Vancomycin Resistant *Enterococcus* | 4 |
| *Yersinia pestis* | 1 |
| *Yersinia pseudotuberculosis* | 1 |
| Total | 328 |

Figure 2:
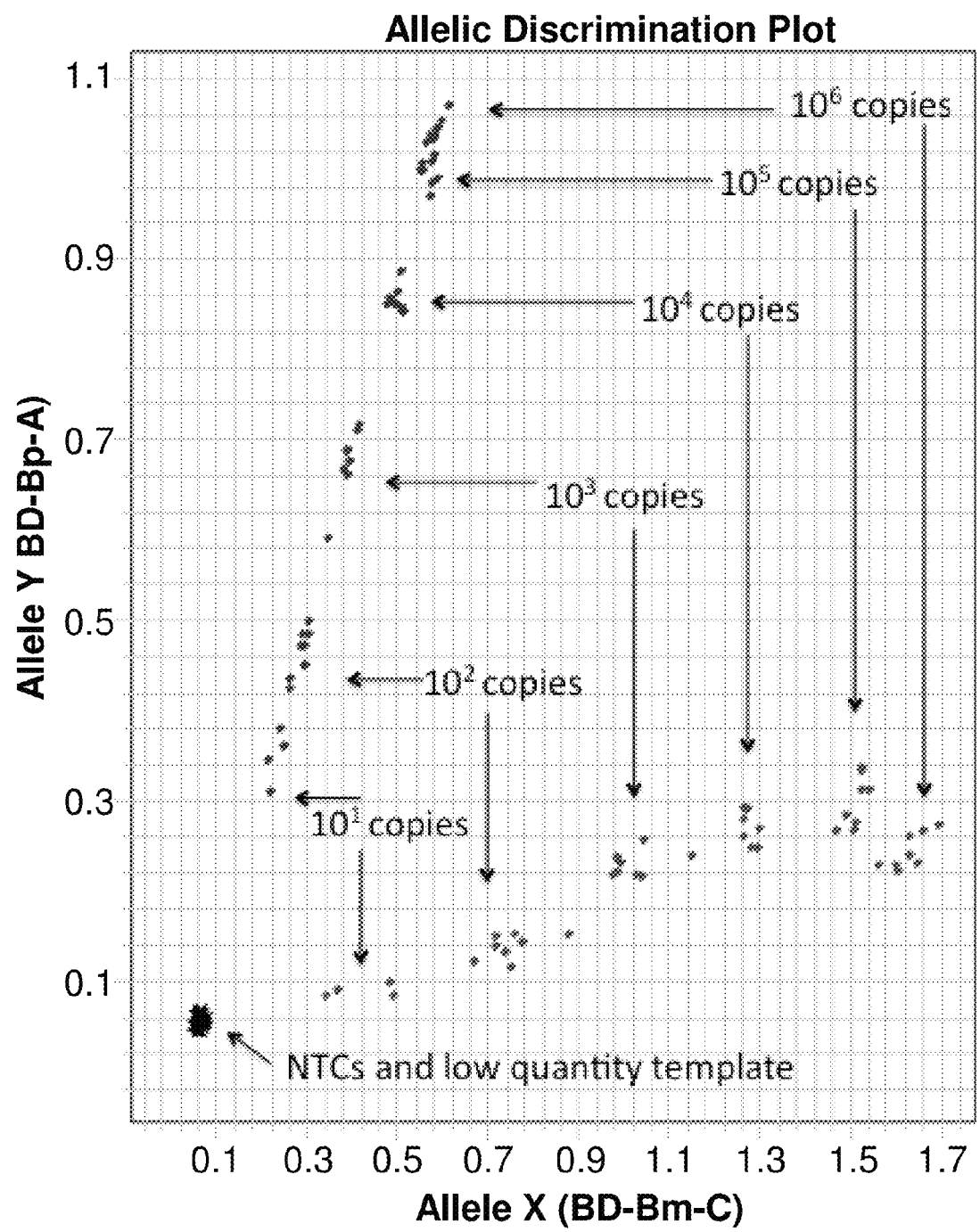

The uniqueness of this region's sequence to *B. pseudomallei* and *B. mallei* according to a GenBank BLAST search, and the short PCR amplicon length (73 bp) make this region conducive to SNP detection by high resolution melt (HRM) analysis. To determine the utility of HRM for allelic discrimination as an alternative to Taqman, HRM was carried out in 10 uL reactions containing 200 nM of each of the above primers, 1× Roche Applied Sciences High Resolution Melt Master, and 2 ng template. Thermal cycling was performed on a Roche LC480. A subset of the collection that includes 45 isolates of *B. pseudomallei*, 23 isolates of *B. mallei*, and 26 isolates of non-target species was genotyped using the HRM assay. It was shown that the HRM assay was also specific to *B. pseudomallei* and *B. mallei*, and successfully differentiated the two species even with genome copies as low as 10 in the samples. FIG. 2 depicts results of 8 replicates of serially diluted *B. pseudomallei* and *B. mallei* using Allelic Discrimination Plot. The test was shown to be sensitive to copy number above 10 in a sample of either the *B. pseudomallei* or the *B. mallei* strains.

Figure 3:
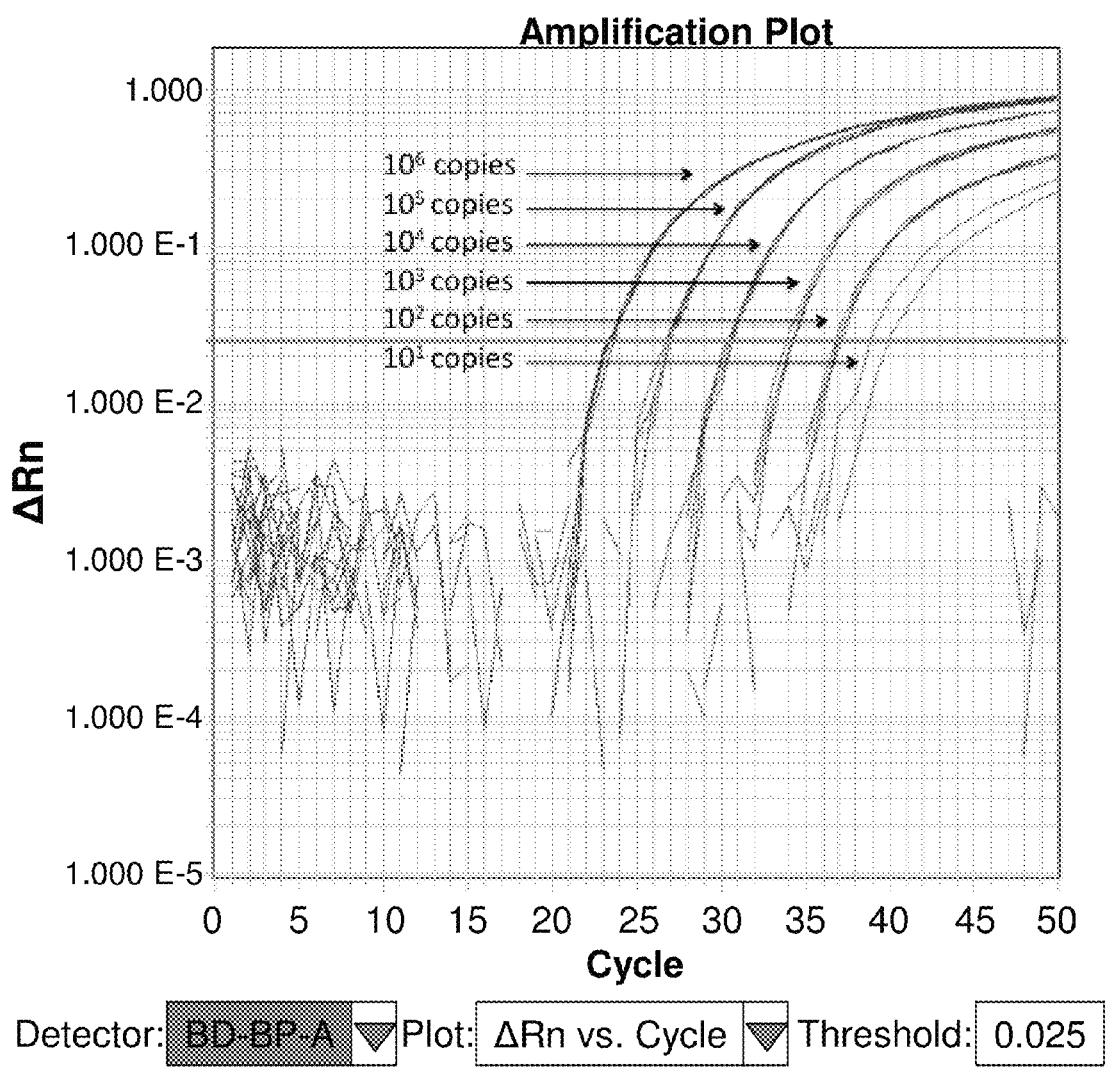
Figure 4:
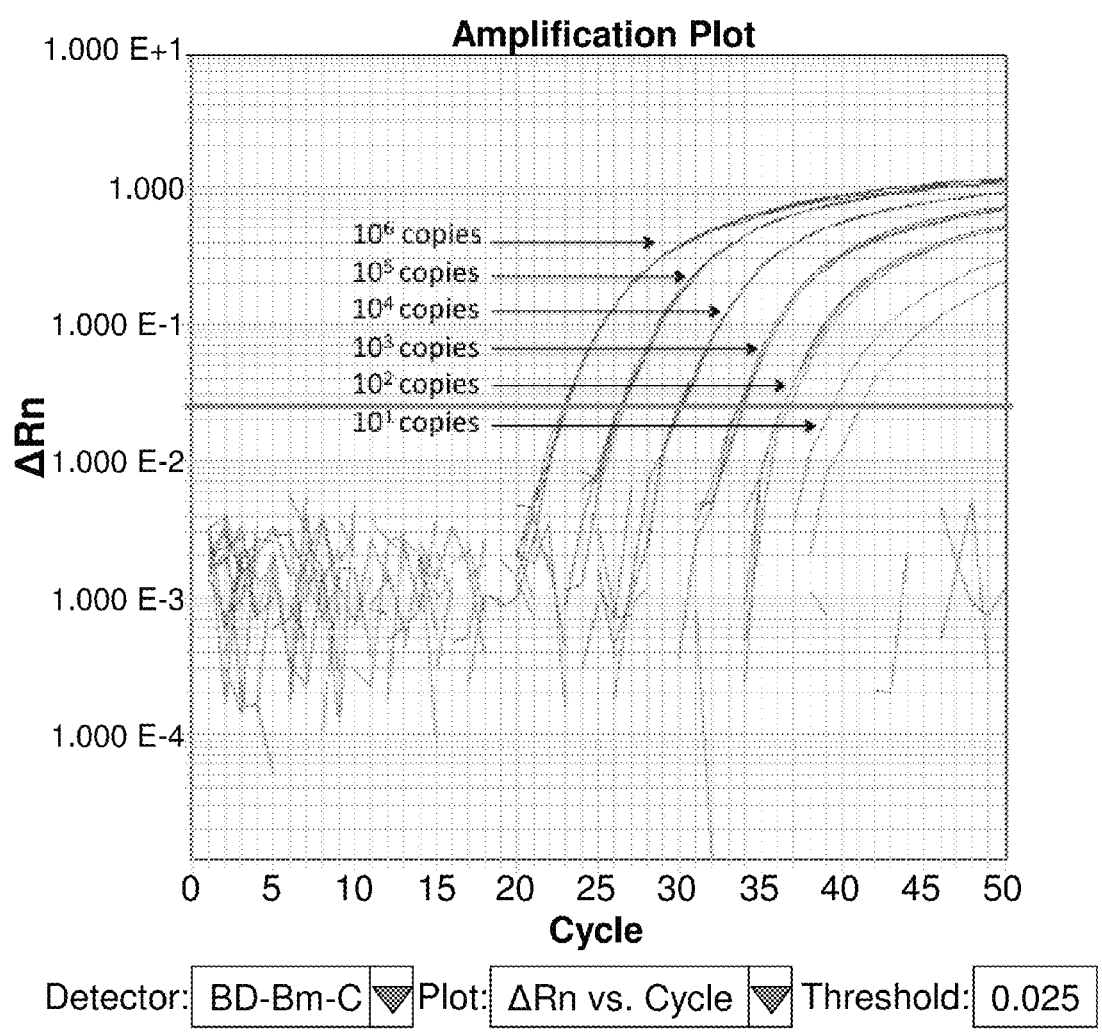

The limit of detection of the Taqman assay was assessed using a dilution series of DNA from isolates of *B. pseudomallei* and *B. mallei*. DNA was quantified using an in-house 16S real-time qPCR assay (unpublished). Template amounts ranging from $10^6$ to $10^0$ genome copies per reaction were used for limit of detection determination. The Taqman limit of detection analysis showed consistent detection and allelic discrimination of *B. pseudomallei* (FIG. 3) and *B. mallei* (FIG. 4) at DNA template levels as low as $10^2$ genome copies with sporadic amplification and genotyping at $<10^2$ genome copies. When the genome copies are lower than $10^2$, the sensitivity of the assay was affected as that 2 of the 4 replicates did not amplify at the $10^1$ copy template for both the *B. pseudomallei* (FIG. 3) and *B. mallei* (FIG. 4).

We claim:

1. A method of determining whether a sample contains *B. mallei* or *B. pseudomallei* comprising the steps of: receiving said sample, wherein said sample comprises nucleic acid; forming a mixture by adding oligonucleotides represented by SEQ ID NO. 1, SEQ ID NO. 2, SEQ ID NO. 3, and SEQ ID NO. 4 to said nucleic acid; subjecting said mixture to conditions that allow amplification of said nucleic acid; and identifying said sample as containing or not containing *B. mallei* or *B. pseudomallei* based upon a result of the nucleic acid amplification.

2. The method of claim 1, further comprising the step of performing DNA sequencing upon one or more products of the nucleic acid amplification.

3. The method of claim 1, wherein said oligonucleotide represented by SEQ ID NO. 3 comprises a first label and wherein said oligonucleotide represented by SEQ ID NO. 4 comprises a second label different from said first label.

4. The method of claim 1, wherein said first oligonucleotide is affixed to a solid substrate.

5. The method of claim 1, wherein said sample comprises an environmental sample.

6. The method of claim 1, wherein said sample is derived from a subject selected from the group consisting of a human, a companion animal, and a livestock animal.

7. The method of claim 1, wherein said result comprises one or more DNA sequences.

8. The method of claim 1, wherein said result comprises one or more ΔCt values.

9. A kit that facilitates determining whether a nucleic acid-containing sample contains *B. mallei* or *B. pseudomallei* comprising:

a first oligonucleotide represented by SEQ ID NO. 1;
a second oligonucleotide represented by SEQ ID NO. 2;
a third oligonucleotide represented by SEQ ID NO. 3;
a fourth oligonucleotide represented by SEQ ID NO. 4; and
an indication of a result that signifies classification of the sample as containing a bacteria selected from the group consisting of *B. mallei* and *B. pseudomallei* when said nucleic acid from said sample is mixed with said first and said second oligonucleotides;
wherein at least the first oligonucleotide is affixed to a substrate, and further wherein the third oligonucleotide comprises a first label and the fourth oligonucleotide comprises a second label different from said first label.

10. The kit of claim 9, wherein said result is in a form selected from the group consisting of a ΔCt value and a nucleic acid sequence.

11. The kit of claim 9, wherein said indication is selected from the group consisting of a positive control, a writing, and software configured to detect the result as input and identification of the sample as containing *B. mallei* or *B. pseudomallei* as output.

\* \* \* \* \*